US00PP12785P2

(12) United States Plant Patent
Trees

(10) Patent No.: US PP12,785 P2
(45) Date of Patent: Jul. 23, 2002

(54) VERBENA PLANT NAMED 'BALWILPURI'

(75) Inventor: Scott Trees, Shell Beach, CA (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 09/822,932

(22) Filed: Mar. 30, 2001

(51) Int. Cl.[7] ..... A01H 5/00
(52) U.S. Cl. ..... Plt./308
(58) Field of Search ..... Plt./308

*Primary Examiner*—Bruce R. Campell
*Assistant Examiner*—Kent L. Bell
(74) *Attorney, Agent, or Firm*—Gardner Carton & Douglas

(57) ABSTRACT

A new and distinct Verbena plant named 'Balwilpuri', characterized by its purple flowers, mounded trailing habit, and dark green leaves.

1 Drawing Sheet

BACKGROUND OF THE INVENTION

The present invention comprises a new and distinct verbena plant, botanically known as *Verbena hybrida*, and hereinafter referred to by the cultivar name 'Balwilpuri'.

The new cultivar was developed by the inventor through a controlled breeding program during 1998, at Arroyo Grande, Calif. The objective of breeding program was the development of verbena cultivars with semi-trailing mounded habit, continuous flowering, excellent basal branching and small dark green foliage.

The female (seed) parent of 'Balwilpuri' was the proprietary verbena cultivar designated PAS36117, which exhibits a semi-trailing growth habit, dark purple flowers and serrated medium green foliage. The male (pollen) parent of Balwilpuri was the commercially available verbena 'SUNVP-SU' (U.S. Plant Pat. No. 10,311) which exhibits a vigorous trailing growth habit, red flowers and dark green foliage.

Asexual reproduction of the new cultivar by terminal stem cuttings in Arroyo Grande, Calif. and West Chicago, Ill. has demonstrated that the characteristics of the new cultivar as herein described are firmly fixed and are retained through successive generations of such asexual propagation.

SUMMARY OF THE INVENTION

It was found that the cultivar of the present invention:

(a) exhibits purple flowers, (b) forms dark green foliage, (c) exhibits a good basal branching character and (d) exhibits an upright mounded and trailing growth habit.

When the new cultivar of the present invention is compared to its male parent, 'SUNVP-SU' it is found that the new cultivar has larger leaves, wider inflorescences and flowers of a bluer color. When compared to 'Temari Violet' (unpatented) it is found that 'Balwilpuri' has larger leaves, smaller flowers and more flowers per inflorescence as detailed in Table A.

BRIEF DESCRIPTION OF THE PHOTOGRAPH

The accompanying photograph illustrates the overall appearance of the new cultivar as true as it is reasonably possible to obtain colored reproductions of this type. Color in the photograph may differ slightly from the color values cited in the detailed botanical description which accurately describe the actual colors of the new Verbena. The photograph depicts typical growth habit and flower color of 'Balwilpuri' with four plants in a pot grown for 12 weeks in West Chicago, Ill., U.S.A.

DETAILED BOTANICAL DESCRIPTION

The 'Balwilpuri' cultivar has not been observed under all possible environmental conditions to date. Accordingly, it is possible that the phenotype may vary somewhat with variations in the environment, such as temperature, light intensity, and day length.

The chart used in the identification of colors described herein is the R.H.S. Colour Chart of The Royal Horticultural Society, London, England. The color values were determined on Aug. 15, 2000. The readings were taken between 1:00 and 3:00 p.m. under natural daylight conditions. The plants used for the descriptions were produced from cuttings taken from stock plants and grown for 8 to 10 weeks in a double poly carbonate covered greenhouse in West Chicago, Ill. under conditions comparable to those used in commercial practice while utilizing a soilless growth medium and maintaining temperatures of approximately 72° F. during the day and approximately 65° F. during the night.

Classification:

*Botanical.*—*Verbena hybrida* cultivar 'Balwilpuri'.

Parentage:

*Female parent.*—Proprietary verbena cultivar PAS36117.

*Male parent.*—'SUNVP-SU'.

Propagation:

*Type cutting.*—Terminal tip.

*Time to initiate roots.*—Approximately 14–21 days with the shorter times generally being experienced in the summer and the longer times in the winter.

*Root description.*—Fibrous, branching.

Plant description:

*Habit of growth.*—Moderately vigorous with good basal branching. Pinching improves basal branching. A mature plant, 8–10 weeks after the planting of a rooted cutting, commonly measures approximately 30 cm in height and 35 cm in width.

*Form.*—Upright mounded and trailing.

*Stem.*—Tetragonal, approximately 2.4 mm in diameter, with dense soft pubescence, 144A. Internode length is approximately 3 cm.

*Foliage.*—Leaves are opposite, ovate with crenate-serrate margin, acute apex and attenuate to oblique base. Texture: Velvety, covered with dense, short soft hairs on upper and lower surface, especially along veins of lower surface. Size: Approximately 3.3 cm in length and approximately 2.2 cm at widest point. Color: Upper surface is between 137A and 139A, lower surface is 137B. Venation: Reticulate, 146D on both upper and lower surface. Petiole: Approximately 4 mm in length, 146D in color.

Flowering description:

*Flowering habit.*—Freely flowering.

*Natural flowering season.*—Spring through autumn.

*Inflorescence type.*—Corymb Size: Approximately 3 cm deep and approximately 5.3 cm in diameter with approximately 22 fully open flowers per inflorescence at any one time.

*Peduncle.*—Approximately 5 cm in length, 2 mm in diameter.

*Petals.*—Five, fused at base, non-overlapping, flat.

*Flower.*—Diameter: Approximately 1.8 cm. Corolla tube length: Approximately 2 cm.

*Calyx.*—1.5 cm in length, 2 mm in diameter, 5 toothed, 5 ribbed, with stipules. Ribs and stipules are 143A, spaces between ribs are 144D (both surfaces).

*Flower color.*—Upper surface, fully opened: Between 80A and 88A. There is a small area of 89D just above the base of each petal. The base of the upper petal, and to a lesser degree the two side petals, is 84C. Whiskers of 155D around the opening of the corolla tube. Lower surface: closest to 86D. Petals fade to close to 83C with age.

*Reproductive organs.*—There are 4 stamens, one pistil 2 cm in length. Pollen color is 2D.

Seed production: Seed production has not been observed.

Disease resistance: Disease resistance has not been observed.

TABLE A

| CHARACTERISTIC | BALWILPURI | 'TEMARI VIOLET' | 'SUNUP-SU' |
|---|---|---|---|
| PLANT HEIGHT - CM | 30 | 27 | 33.2 |
| INERNODE LENGTH - CM | 3 | 2.5 | 2.1 |
| STEM COLOR | 144A WITH NO ANTHOCYANIN COLORATION | 143A WITH NO ANTHOCYANIN COLORATION | 144A WITH PURPLE ANTHOCYANIN COLORATION ALONG EDGES |
| PETIOLE LENGTH - MM | 4 | 3 | 3 |
| LEAF LENGTH × WIDTH | 3.3 × 2.2 | 2 × 1.4 | 2.2 CM × 1.5 CM |
| INFLORESCENCE LENGTH × WIDTH - CM | 3 × 5.3 | 2.9 × 4.3 | 3.9 × 4 |
| FLOWER COLOR - UPPER SURFACE - RHS | BETWEEN 80A AND 88A AT APEX; 89D AT BASE | 84A AT APEX; 85B AT BASE | 44B AT APEX; 45A AT BASE |
| CALYX COLOR | RIBS OF 143A; 144D BETWEEN RIBS (BOTH SURFACES), NO ANTHOCYANIN | UNAVAILABLE | RIBS OF 143A; 144D BETWEEN RIBS WITH PURPLE ANTHOCYANIN COLORATION IN TWO SPOTS ALONG RIM |

I claim:

1. A new and distinct cultivar of *Verbena hybrida* plant named 'Balwilpuri' substantially as herein shown and described, which:

(a) exhibits purple flowers, (b) forms dark green foliage, (c) exhibits a good basal branching character and exhibits a mounded and trailing growth habit.

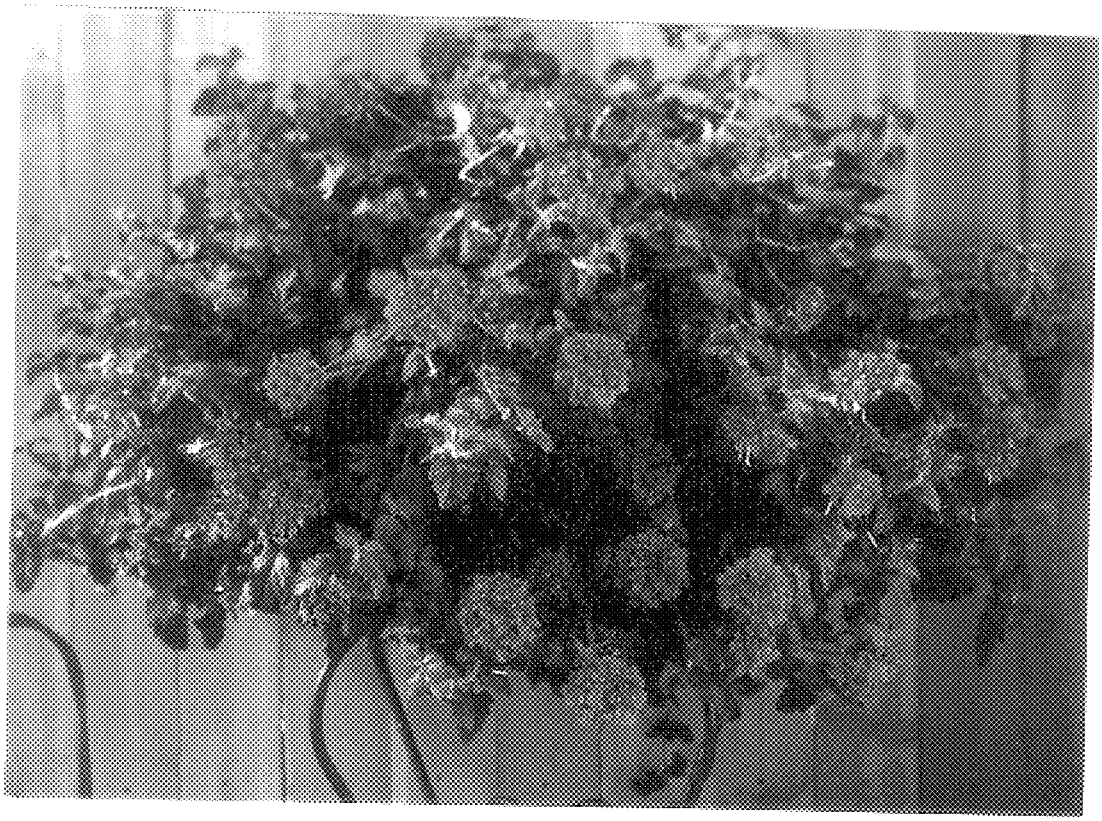

* * * * *